(12) United States Patent
Counsell et al.

(10) Patent No.: US 7,582,279 B2
(45) Date of Patent: *Sep. 1, 2009

(54) BLOOD-POOL CARRIER FOR LIPOPHILIC IMAGING AGENTS

(75) Inventors: Raymond E. Counsell, Ann Arbor, MI (US); Marc A. Longino, Ann Arbor, MI (US); Jamey P. Weichert, Ann Arbor, MI (US)

(73) Assignee: The Board of Regents of the University of Michigan, Ann Arbor, MI (US)

( * ) Notice: Subject to any disclaimer, the term of this patent is extended or adjusted under 35 U.S.C. 154(b) by 207 days.

This patent is subject to a terminal disclaimer.

(21) Appl. No.: 10/692,311

(22) Filed: Oct. 23, 2003

(65) Prior Publication Data

US 2004/0258744 A1 Dec. 23, 2004

Related U.S. Application Data

(63) Continuation of application No. 09/058,715, filed on Apr. 10, 1998, now Pat. No. 6,645,463, which is a continuation-in-part of application No. 08/243,596, filed on May 16, 1994.

(60) Provisional application No. 60/043,305, filed on Apr. 11, 1997.

(51) Int. Cl.
*A61K 51/00* (2006.01)
*A61M 36/14* (2006.01)

(52) U.S. Cl. ............... 424/1.29; 424/1.11; 424/1.13; 516/53

(58) Field of Classification Search ............ 424/1.11, 424/1.13, 9.1, 9.3, 9.4, 400, 484, 1.65, 1.45, 424/1.21; 516/53
See application file for complete search history.

(56) References Cited

U.S. PATENT DOCUMENTS

| 4,873,075 A | 10/1989 | Counsell et al. |
| 4,957,729 A | 9/1990 | Counsell et al. |
| 5,043,164 A | 8/1991 | Huang et al. |
| 5,093,042 A | 3/1992 | Counsell et al. |
| 5,116,599 A | 5/1992 | Rogers, Jr. et al. |
| 5,234,680 A | 8/1993 | Rogers, Jr. et al. |
| 5,326,552 A | 7/1994 | Na et al. |
| 5,478,860 A | 12/1995 | Wheeler et al. |
| 5,543,158 A | 8/1996 | Gref et al. |
| 5,851,510 A * | 12/1998 | Counsell et al. ............ 424/9.45 |
| 6,126,946 A * | 10/2000 | Counsell et al. ............. 424/401 |
| 6,214,375 B1 * | 4/2001 | Modi ......................... 424/450 |
| 6,645,463 B1 * | 11/2003 | Counsell et al. ............ 424/1.21 |

FOREIGN PATENT DOCUMENTS

| DE | 44 08 011 C1 | 11/1995 |
| WO | WO 93/19738 | 10/1993 |
| WO | WO 94/07466 | 4/1994 |
| WO | WO 95/31181 | 11/1995 |
| WO | WO 96/34598 | 11/1996 |
| WO | WO 97/13499 | 4/1997 |
| WO | WO 97/40858 | 11/1997 |

OTHER PUBLICATIONS

Wheeler et al (Journal of Pharmaceutical Sciences, 1994, vol. 83, No. 11, pp. 1558-1564).*

Counsell, et al., "Principles of Medicinal Chemistry, 4th Edition," edited by William Foye, Chapter 45, 1995.

Liu, et al., "Long-Circulating Emulsions (Oil-in-Water) as Carriers for Lipophilic Drugs," *Pharm. Res.*, 12: 1060-1062 (1995).

*Handbook of Chemistry and Physics*, 58th Edition, pp. B-303-305, CRC Press, 1977-1978.

Kirpotin, et al., "Liposomes With Detachable Polymer Coating: Destabilization and Fusion of Dioleoylphosphatidylethanoloamine Vesicles Triggered by Surface-Grafted Poly(ethylene Glycol)," *FEBS Letters*, 388:115-118 (1996).

Sachse, et al., "Biodistribution and Computed Tomography Blood-Pool Imaging Properties of Polyethylene Glycol-Coated Iopromide-Carrying Liposomes," *Invest. Radio.*, 32(1):44-50 (1997).

Schneider, et al., "Surface Modification of Continuously Extruded Contrast-Carrying Liposomes: Effect on Their Physical Properties," *International Journal of Pharmaceutics*, 132:9-21 (1996).

Scherphof, et al., "Intrahepatic Distribution of Long-Circulating Liposomes Containing Poly(Ethylene Glycol) Distearoyl Phosphatidylethanolamine," *Journal of Liposome Research*, 4(1):213-228 (1994).

(Continued)

*Primary Examiner*—D L Jones
(74) *Attorney, Agent, or Firm*—Morgan, Lewis, and Bockius, LLP (57) ABSTRACT

A surface-modified lipoprotein-like oil-in-water emulsion useful as a blood-pool selective delivery vehicle for lipophilic imaging agents or lipophilic derivatives of water-soluble imaging agents. The blood-pool selective delivery vehicle remains in the blood for several hours, shows very little early hepatic sequestration, and is cleared from the blood within 24 hours. The mean diameter of the oil phase is less than 150 nm which minimizes sequestration by the reticuloendothelial system. The surface of the oil phase is modified with a polyethyl glycol-modified phospholipid to prevent normal interactions with the receptor sites of the hepatocytes. In radiographic imaging, radioactive or stable, synthetic or semi-synthetic polyhalogenated triglycerides, such as 2-oleoylglycerol-1,3-bis[7-(3-amino-2,4,6-triiodophenyl) heptanoate], or lipid soluble derivatives of traditional water-soluble contrast agents, such as aliphatic esters of iopanoic, diatrizoic, and acetrizoic acid, may be incorporated into the lipophilic core of a lipoprotein-like emulsion particle.

90 Claims, 4 Drawing Sheets

OTHER PUBLICATIONS

Weichert, et al., "Potential Tumor-or Organ-Imaging Agents. 26. Polyiodinated 2-Substituted Triacylglycerols as Hepatographic Agents," *J. Med. Chem.*, 29:1674-1682 (1986).

Weichert, et al., "Potential Tumor- or Organ-Imaging Agents. 27. Polyiodinated 1,3-Disubstituted and 1,2, 3-Trisubstituted Triacylglycerols," *J. Med. Chem.* 29:2457-2465 (1986).

Weichert, et al., "Polyiodinated Triglyceride Analogs as Potential Computer Tomography Imaging Agents for the Liver," *J. Med. Chem.*, 38:636-646 (1995).

Wheeler, et al., "Polyethylene Glycol Modified Phospholipids Stabilize Emulsions Prepared From Triacylglycerol," *J. Pharm. Sci.*, 83:1558-1564 (1994).

* cited by examiner

WHERE R IS A STRAIGHT OR BRANCHED CHAIN LOWER ALKYL,
$-CH_2-(CH)_n-CH_3$ ; n=0-16

BLOOD-POOL CARRIER FOR LIPOPHILIC IMAGING AGENTS

CROSS REFERENCE TO RELATED APPLICATIONS

This application is a continuation of U.S. patent application Ser. No. 09/058,715 filed Apr. 10, 1998, now U.S. Pat. No. 6,645,463, which is a continuation-in-part of U.S. patent application Ser. No. 08/243,596 filed on May 16, 1994, now U.S. Pat. No. 5,851,510, which claims priority under 35 U.S.C. 119(e) to U.S. Provisional Patent Application No. 60/043,305, filed Apr. 11, 1997, each of which are hereby incorporated herein by reference in their entirety for all purposes.

BACKGROUND OF THE INVENTION

This invention relates generally to an oil-in-water emulsion, and more particularly, to an oil-in-water emulsion that functions as a blood-pool selective carrier or delivery vehicle for lipophilic imaging agents, or lipid-soluble derivatives of water-soluble, imaging agents incorporated therein.

Conventional water-soluble contrast media for x-ray computed tomography (CT) and magnetic resonance imaging (MRI) rapidly diffuse out of the blood following injection. Vascular imaging, for example, therefore depends on invasive intra-arterial infusion of large amounts of contrast media at or near the suspected site of disease. Despite administration of a bolus dose of contrast media, enhancement lasts for only a few seconds. In CT angiography, as a specific example, a large amount (<200 ml) of a conventional water-soluble urographic agent is administered directly into the artery at a rate approaching 5 ml/sec. Such rapid administration can cause nausea and vomiting. Because conventional urographic agents are rapidly distributed throughout the vascular space before rapid renal elimination, CT scanning must be accomplished within 30 seconds of administration while the agent is still in the circulation phase. Intravascular contrast is rapidly lost as the agent diffuses into the extravascular space and distributes nonspecifically throughout the body. There is, therefore, a need for a delivery vehicle for CT scanning that can be administered less invasively and that will prolong the presence of the agent in the blood.

Several experimental CT agents have been developed to provide extended circulation time in the blood, including high molecular weight carboxymethyl dextrans and nanocrystalline particulates. Iodinated versions of the dextrans have opacified blood for up to 20 minutes, however, significantly delayed clearance (greater than a day) from the liver poses a concern. The nanocrystalline particulates comprising, in one example, solid ethyl diatrizoate having a particle size ranging from 200-400 nm, are also very slowly cleared by the reticuloendothelial system (RES) of the liver and spleen. There is, thus, a need for a delivery vehicle that will circulate in the blood for a prolonged period of time, but which will be metabolized and cleared from the system within an acceptable time period.

In addition to the foregoing experimental agents, several liposomal oil-in-water emulsions have been developed wherein the inclusion of polyethylene glycol (PEG) or a PEG derivative of a phospholipid, was found to reduce RES uptake and clearance of parenterally administered delivery vehicles and to prolong the blood half life of the vehicles. Although liposomes and lipoproteins share some common structural lipid components and have considerable overlap in particle size, there remain significant differences in particle structure and in the mechanism of sequestration of the two particle types by their respective target tissues.

Liposomes, which are artificially prepared lipid vesicles formed by single or multiple polar lipid bilayers, consisting primarily of phospholipids and cholesterol, enclosing aqueous compartments are particulate in nature, and hence, have potential for delivering agents contained therein to the RES. Investigators have attempted to load liposomes with both ionic and non-ionic water-soluble urographic contrast media. However, stabilization of the resulting liposome against loss of contrast media from the bilayers has proven to be a major problem. Moreover, incorporation of neutral lipophilic agents into the bilayer is limited by the low capacity of the lipophilic agents to become incorporated in the membrane matrix and the restricted loading capacity of the liposome.

Lipoproteins, on the other hand, are naturally-occurring, oil-in-water emulsions composed of a monolayer of polar (amphiphilic) lipids that surround a neutral lipid core made up of cholesteryl esters and triglycerides. A variety of apolipoproteins associate with the polar monolayer of these lipid-transport particles. Each of the apolipoproteins plays a role as a recognition factor for tissue-selective, receptor-mediated uptake or in enzyme-mediated metabolism of the various classes of lipoproteins. Liposomes, which lack these specific surface recognition proteins, are rapidly sequestered by macrophages of the RES in the lungs, liver (Kupffer cells), spleen, and bone marrow. Liposomal biodistribution can be modulated somewhat by alteration of the surface charge, particle size, and chemical modification of surface components, although a significant portion of the modified liposomal material is still sequestered by the macrophages. A problem with RES-mediated particulates, such as the aforementioned liposomes is toxicity. Large imaging doses of particulate contrast agents have been associated with engorgement of the Kupffer cells of the liver resulting in sinusoidal congestion and consequent activation of macrophages which release toxic mediators.

Accordingly, there remains a great need in the art for less toxic delivery vehicles or compositions, including contrast-producing oil-in-water emulsions for diagnostic purposes that have prolonged blood circulation time, yet are cleared from the system within a reasonable period of time.

It is, therefore, an object of this invention to provide a delivery vehicle, specifically a blood-pool selective, surface-modified, oil-in-water emulsion, for transport of lipophilic agents, or lipophilic derivatives of water soluble agents, such as radiologic contrast agents.

It is another object of the invention to provide a blood-pool selective delivery vehicle, specifically a lipoprotein-like oil-in-water emulsion, that achieves prolonged retention in the circulation by avoiding sequestration by the RES.

It is still another object of this invention to provide a blood-pool selective delivery vehicle that is substantially free of liposomal contamination.

It is also an object of this invention to provide a delivery vehicle, specifically a blood-pool selective, surface-modified, oil-in-water emulsion, that remains in the blood for a prolonged period of time (on the order of 1 to 2 hours versus seconds) following intravenous administration (versus invasive arterial catheterization).

SUMMARY OF THE INVENTION

The foregoing and other objects are achieved by this invention which is a surface-modified synthetic oil-in-water lipid emulsion, resembling endogenous lipoproteins, in order to take advantage of the natural lipid transport system of a living being. The surface-modified oil-in-water emulsion of the present invention have been modified with derivatized polyethylene glycol or polyethylene glycol derivatives of phospholipids to prolong retention time in the blood, possibly by interfering with the association of the emulsion particles with apolipoproteins and/or opsonins which are responsible for mediating cellular uptake and circulatory elimination of the vehicle. Lipophilic agents or lipophilic derivatives of water-soluble agents which are diagnostically, therapeutically, or biologically active or inactive, inserted into the lipid core of the emulsion are retained in the blood.

In accordance with the present invention, the mean oil phase particle size is between 50 and 150 nm (number weighted), with a narrow size distribution (50 to 250 nm) wherein no more than 2% of the particles have a diameter that falls outside of the range (i.e., being greater than 250 nm). The emulsion should have no detectable particles with a diameter greater than 1 μm. Moreover, the emulsion should not be contaminated with liposomes.

In a composition aspect of the invention, the synthetic oil-in-water emulsion of the present invention has the general formula:
1. up to 50% lipophilic core components (w/v);
2. up to 10% emulsifier (w/v);
3. up to 5% cholesterol (w/v);
4. up to 5% derivitized PEG or PEG-derivative of a phospholipid (w/v):
5. up to 5% osmolarity adjusting agent (w/v);
6. optionally, up to 1% antioxidant (w/v); and
7. water to final volume.

The types of agents that can be administered by incorporation into the lipophilic core of the synthetic oil-in-water emulsions of the present invention are lipophilic contrast agents and/or lipophilic derivatives of conventional water-soluble contrast agents. The lipophilic core components comprise up to 50% (w/v) of the emulsion, and preferably between about 10% and 40% (w/v). The lipophilic core may comprise any pharmaceutically acceptable fat or oil of natural, synthetic, or semi-synthetic origin which is a pharmacologically inert nonpolar lipid that will locate in the lipophilic core of the oil-in-water emulsion. Specific examples include, without limitation, triglycerides, illustratively, triolein, a naturally-occurring triglyceride of high purity (available from a variety of commercial sources, such as Sigma Chemical Company, St. Louis, Mo.), or oils of animal or vegetable origin, such as soybean oil, safflower oil, cottonseed oil, canola oil, fish oils, and other biocompatible oils.

In preferred embodiments, the lipophilic core includes lipophilic contrast agents or lipophilic derivatives of water-soluble contrast agents that may be used for diagnostic purposes. For diagnostic purposes, exemplary agents include, but are not limited to, halogenated triglycerides, such as iodinated or fluorinated triglycerides; perfluorinated lower alkyls; or aliphatic esters of conventional water-soluble contrast agents, such as aliphatic esters of iopanoic acid, which agents may contain a stable or radioactive isotope of the halogen. The term "contrast agent" or "imaging agent" is used herein to denote generically an agent useful for any imaging modality.

In particularly preferred embodiments, the lipophilic core includes a mixture of at least one pharmacologically inert (or inactive) oil and a contrast agent in a molar ratio in the range of 0.1 to 3. On a weight/weight (w/w) basis, the ratio of inert oil to contrast agent is from 0.1:1.0 to 2:1, and more preferably 1:1. Preferably, the lipophilicity of each core component is comparable to ensure suitable blending of the lipid components.

In iodinated embodiments, iodine-containing lipids, of the type known in the art, can be used. Such lipids include iodinated fatty acids in the form of glycerol or alkyl esters. However, in particularly preferred embodiments, the iodine-containing lipids are synthetic aromatic compounds of known purity that are stabilized against in vivo degradation of the iodine linkage. Illustrative examples of radioactive or non-radioactive halogenated triglycerides useful in the practice of the invention include, without limitation, iodinated triglycerides of the type described in U.S. Pat. No. 4,873,075 issued on Oct. 10, 1989; U.S. Pat. No. 4,957,729 issued on Sep. 18, 1990; and U.S. Pat. No. 5,093,043 issued on Mar. 3, 1992. Exemplary iodinated triglycerides are 2-oleoylglycerol-1,3-bis[7-(3-amino-2,4,6-triiodophenyl)heptanoate] (DHOG) and 2-oleoylglycerol-1,3-bis[4-(3-amino-2,4,6-triiodophenyl)butanoate] (DBOG), such as disclosed in International Publication No. WO 95/31181 published Dec. 14, 1995, the text of which is incorporated herein by reference.

Clinically, $^{123}$I, $^{125}$I, and $^{131}$I are the iodine isotopes most often used with currently available scanning instrumentation. Of course, $^{131}$I-radiolabeled triglycerides may be used for therapeutic purposes, as is known in the art. However, any radioactive isotope of iodine is within the contemplation of the invention. A listing of all iodine isotopes is available, for example, at pages Misc. 47-49 of the Merck Index, 11$^{th}$ Edition, and at pages 11-68 to 11-70 of the *Handbook of Chemistry and Physics,* 72d Edition, CRC Press, 1991-1992. It should be noted that $^{127}$I is the naturally-occurring stable isotope and is not considered to be "radioactive".

In fluorinated embodiments, specific examples include stable ($^{19}$F) or radioactive ($^{18}$F) fluorinated triglycerides that are analogous to the iodinated triglycerides discussed above, illustratively glyceryl-2-oleoyl-1,3-bis(trifluoromethyl)phenyl acetate. In alternative embodiments of the invention, fluorine-containing lipids may be esters or triglycerides of perfluoro-t-butyl-containing fatty acid compounds, such as described in U.S. Pat. Nos. 5,116,599 and 5,234,680, illustratively, 7,7,7-trifluoro-6,6-bis (trifluoromethyl)-heptanoic acid or 8,8,8-trifluoro-7,7-bis(trifluoromethyl)-octanoic acid. Other examples include the perfluorinated low molecular weight hydrocarbons, useful as ultrasound imaging agents, such as described in U.S. Pat. No. 5,716,597.

In still further embodiments of the invention, the contrast agent may comprise brominated compounds, such as brominated ethyl esters of fatty acids or monobrominated perfluorocarbons. Of course, these examples are merely illustrative of the many specific examples of lipophilic compounds suitable for use in the practice of the invention, and are not in any way intended to be exclusive or limiting.

While the invention is described in terms of the delivery of diagnostic contrast agents, it is to be understood that therapeutic agents, specifically radiopharmaceuticals, may be included in the lipophilic core of the synthetic oil-in-water emulsion of the present invention.

The monolayer surrounding the nonpolar lipophilic core comprises up to about 10% (w/v) of an amphipathic lipid monolayer component, which may be an emulsifier. Phospholipids of natural, synthetic, or semi-synthetic origin are suitable for use in the practice of the invention. Traditional lipid emulsions for delivery of contrast agents use natural phospholipids, such as soy lecithin and egg phosphatidylcholine (e.g., Intralipid). In preferred embodiments of the present invention, the emulsion components are synthetic, semi-synthetic, and/or naturally occurring components of known origin, purity and relative concentrations. The improper use of egg lecithins (mixtures of phospholipids) and/or crude oils (cottonseed, poppy seed, and the like), as in typical prior art emulsions, may result in variable and non-reproducible compositions.

In a specific advantageous embodiment, dioleoylphosphatidylcholine (DOPC) is used as an emulsifier, or monolayer surfactant. DOPC is a semi-synthetic, chemically defined phospholipid emulsifier of high purity (available from Avanti Polar Lipids, Alabaster, Ala.). Of course, other surface active agents that are suitable for parenteral use can be substituted for all or a portion of the polar lipid monolayer component. The naturally-occurring phospholipids are advantageous because these phospholipids are biocompatible and have an appropriate phase transition temperature, i.e., they are in the liquid state at physiologic temperatures.

In addition to the foregoing, polyethylene glycol-linked lipids are incorporated into the monolayer. A derivatized polyethylene glycol, such as methoxy polyethylene glycol (MPEG), having a molecular weight between about 1000 and 6000 and/or polyethylene glycol-derivatized lipids, such as MPEG-linked to phosphatidylethanolamine or distearoyl phosphatidylethanolamine are preferred. The PEG component should comprise between about 0.1 and 30 mole percent of the monolayer components for achieving atteniation of retention time of the delivered contrast agent in the blood.

In preferred embodiments, the synthetic MPEG-linked phospholipids may contain fatty acyl groups, including but not limited to myristoyl, palmitoyl, steroyl, oleoyl, or combinations thereof. MPEGs can be covalently linked to the phospholipid moiety by succinate, carbamate, or amide linkages, or by other covalent linkages known to those skilled in the art. MPEG-linked phospholipids are available commercially from Matreya, Inc., Pleasant Gap, Pa. and Avanti Polar Lipids, Inc., Alabaster, Ala. Preferred MPEG-modified phospholipids include MPEG-linked phosphatidylethanolamine; MPEG-2000-1,2-distearoyl; and MPEG-2000-1,2-dioleoyl phosphatidylethanolamine. Of course, other polysaccharides can be associated with phospholipids, or other suitable membrane lipid moieties, to modify the surface of the monolayer in order to block association of the emulsion particles with apolipoproteins and/or opsonins, thereby interfering with receptor-mediated uptake and prolonging the residence time of the lipid emulsion in the blood.

The composition also contains a sterol, which is preferably cholesterol, in an amount of up to 5% by weight in order to stabilize the emulsion, and preferably in the range of 0.4 to 0.5% (w/v). In accordance with preferred embodiments of the invention, the molar ratio of sterol to emulsifier, which may be a natural, synthetic, or semi-synthetic phospholipid, has been found to directly affect the particle diameter and dimensional stability. The preferred molar ratio of sterol to phospholipid for achieving an emulsion of the desired size in the range of 0.05 to 0.70, and more specifically at 0.40 for delivery of iodinated triglycerides.

The remainder of the emulsion formulation comprises the bulk or aqueous phase containing up to 5% (w/v) USP glycerol. In the practice of a preferred embodiment of the present invention, the aqueous phase is de-ionized water of a grade suitable for parenteral administration. The inclusion of salt (NaCl), such as by the use of 0.9% saline, or ionic buffers, in the aqueous phase results in unstable emulsions that have a mean particle diameter as much as twice the size of salt-free emulsions. Furthermore, the presence of salt in the formulation has an adverse effect on the ability of the emulsion to survive autoclave sterilization without a significant change in mean particle size as well as on the temporal stability of an autoclaved emulsion. Any ionic species in the formulation adversely impacts the long term stability of the emulsion.

Other conventional additives, such as antioxidants, buffers, preservatives, viscosity adjusting agents, and the like, may be included in the composition. In particular, up to 1% w/v of an antioxidant, such as α-tocopherol, flavinoids, BHT, or BHA, is recommended. However, the additive should not adversely affect the physical and biological characteristics of the emulsion, such as particle size, shelf stability, and biodistribution.

The techniques used to formulate the oil-in-water emulsions of the present invention are important in achieving small particle diameter, uniform size distribution, lack of liposome contamination, etc.

In accordance with a method of making aspect of the invention, the lipophilic components of the oil-in-water emulsion including nonpolar core lipids, polar lipid emulsifiers, and other lipophilic components, such as contrast agents, are blended together to form a premixed lipid phase. The aqueous components are combined and added to the premixed lipid phase. The premixed lipid phase and aqueous components are homogenized to form a crude oil-in-water emulsion. The crude oil-in-water emulsion is subjected to ultra high energy emulsification to produce a fine oil-in-water emulsion having a mean particle diameter of the oil phase between 50 to 150 nm with greater than 98% of the particles being less than 250 nm. In preferred embodiments of the invention, the fine oil-in-water emulsion is sequentially filtered.

In a preferred method aspect of the invention, the lipid components are initially blended or homogenized with USP glycerol using a high speed mixer, such as a Polytron homogenizer (Kinematica GmbH, Lucerne, Switzerland) or Ultra Turrax (IKA-Works, Cincinnati, Ohio), operating at 12,500 rpm under a nitrogen atmosphere at 55° C. for at least 5 minutes. Then, the aqueous components are added to the anhydrous glycerol-lipid emulsion and emulsified by high speed mixing or homogenization at 25,000 rpm under the same, or similar, conditions to form a crude oil-in-water emulsion. Final processing is accomplished with ultra high energy mixing equipment, such as a MicroFluidizer high pressure homogenizer (Model 110S, Microfluidics Corp., Newton, Mass., see. U.S. Pat. No. 4,533,254), or equivalent equipment, such as the Emulsitlex (Avestin Inc., Ottawa, Ontario, Canada) or the Manton-Gaulin (APV Gaulin Rannie, St. Paul, Minn.), operating in the recycling mode at 35-60° C. and 10,000 to 30,000 psi, and preferably at about 14,700-23,000 psi, for up to about 20 minutes. After processing, the emulsion is passed sequentially through sterile 0.45 μm and 0.22 μm sterile filters. The sequential filtration removes any large particles and offers the potential of end-point sterilization of the product.

The temperature for high energy mixing is illustrative, and should be chosen relative to the contrast agent. In other words, the temperature should be greater than or equal to the phase transition temperature or melting point of the contrast agent or emulsifier (phospholipid or MPEG-linked phospholipid). An upper bound, however, is determined by whether the temperature would cause degradation or decomposition of any components in the composition.

The use of an ultra high pressure homogenizer ensures small particle size with a narrow size range distribution. Conventional systems for forming emulsions, such as homogenizers, sonicators, mills, and shaking systems provide a shearing force on the liquid components whereas the ultra high energy mixing equipment puts the emulsion components under pressure and forces them through small openings to reduce particle size. Size distribution may be measured by submicron laser photon correlation spectroscopy (PCS) on a Nicomp 370 Dynamic Laser Light Scattering Autocorrelator (Nicomp Particle Sizing Systems, Santa Barbara, Calif.) or similar equipment. A lipid emulsion, which is suitable for the practice of the present invention, will have a mean particle diameter less than about 250 nm, and preferably in the range of 50 to 150 nm as measured by Nicomp number weighting analysis. The particles should have a narrow size distribution, with about 98% of the particles being in the 50 to 250 nm. No particles should be detected with a diameter of greater than 1 μm.

In a method of use aspect of the invention, an oil-in-water emulsion of the present invention containing a contrast enhancing agent is administered to a mammal and the mammal is subjected to x-ray computed tomographic imaging after the emulsion has reached stable blood levels, e.g., 1-30 minutes post-injection and prior to decline in levels (up to about 2 hours). In alternative methods of use, appropriate oil-in-water emulsions, containing contrast agents suitable for other diagnostic modalities, such as proton magnetic resonance imaging (MRI), $^{19}$F-MRI, ultrasonography, or scintigraphy may be administered for visualization and/or detection.

BRIEF DESCRIPTION OF THE DRAWING

Comprehension of the invention is facilitated by reading the following detailed description, in conjunction with the annexed drawing, in which.

DETAILED DESCRIPTION OF THE INVENTION

The oil phase particle of the present invention has a lipophilic lipid core surrounded by a monolayer consisting of an emulsifier, which may be a phospholipid, a stabilizer, such as cholesterol, the polyethylene glycol-derivatized component. The lipid core contains a pharmacologically inert fat or oil, such as a triglyceride (e.g., triolein) and/or a lipophilic agent, such as a radiologic contrast agent, or a lipophilic derivative of a water-soluble contrast agent. The polar moieties (e.g., polar head portions of a phospholipid emulsifier) of the monolayer face outward into the bulk water phase whereas the nonpolar moieties (tails of the phospholipid emulsifier) of the monolayer are oriented toward the lipid core. A purely lipophilic compound to be delivered in accordance with the principles of the invention would reside almost entirely in the core of the lipid particle beneath the monolayer.

Exemplary lipophilic contrast agents include, but are not limited to, agents of the type reported by Weichert, et al. (see, for example, Weichert, et al., *J. Medicinal Chemistry* (1986, 29:1674-82); (1986, 29:2457-65); and (1995, 38:636-46)) as well as other lipid soluble derivatives of traditional water-soluble contrast agents including, but not limited to, aliphatic esters of iopanoic, diatrizoic, and acetrizoic acids as listed in "Principles of Medicinal Chemistry (4$^{th}$ edition)," edited by William Foye, Chapter 43, R. E. Counsell and J. P. Weichert authors, Williams and Wilkins, 1995.

Illustrative examples of radioactive or non-radioactive polyhalogenated triglycerides particularly suitable for use in the practice of the invention are described in U.S. Pat. No. 4,873,075 issued on Oct. 10, 1989; U.S. Pat. No. 4,957,729 issued on Sep. 18, 1990; and U.S. Pat. No. 5,093,043 issued on Mar. 3, 1992, the disclosures of which are incorporated by reference herein in their entirety. The iodinated arylaliphatic triglyceride analogs of the aforementioned patents have a triglyceride backbone structure that is 1,3-disubstituted or 1,2,3-trisubstituted with a 3-substituted 2,4,6-triiodophenyl aliphatic chain or a monoiodophenyl aliphatic chain. In preferred embodiments, all of the aliphatic chains, whether on the iodinated moiety or an open position on the triglyceride backbone structure, are saturated or unsaturated aliphatic hydrocarbon chains of the type found in naturally-occurring fatty acids. Naturally-occurring fatty acids may include those containing about 4-20 carbons, illustratively palmitic acid (16), palmitoleic acid (16:1), oleic acid (18:1), linoleic acid (18:2), arachidonic acid (20:4), etc.

Specific examples include, but are not limited to: glyceryl-2-palmitoyl-1,3-di-(3-amino-2,4,6-triiodophenyl)iopanoate: glyceryl-2-palmitoyl-1,3-di-(3-amino-2,4,6-triiodophenyl) dodecanoate; glyceryl-2-palmitoyl-1,3-di-(3-amino-2,4,6-triiodophenyl)acetate; glyceryl-2-palmitoyl-1,3-di-(3-amino-2,4,6-triiodophenyl)propionoate; glyceryl-1,2,3-triiopanoate; glyceryl-1,2,3-tri-12-(3-amino-2,4,6-triiodophenyl)dodecanoate; glyceryl-1,3-di-17-(3-amino-2,4,6-triiodophenyl)heptadecanoate; glyceryl-1,2,3-tri-3-(3-amino-2,4,6-triiodophenyl)propionate; glycerol-2-palmitoyl-1,3-di-15-(p-iodophenyl)pentadecanoate; glyceryl 2-oleoyl-1,3-di-(3-amino-2,4,6-triiodophenyl)-butyrate; glyceryl-2-oleoyl-1,3-di-(3-amino-2,4,6-triiodophenyl)-pentanoate, glyceryl 2-oleoyl-1,3-di-(3-amino-2,4,6-triiodophenyl)-hexanoate; glyceryl 2-oleoyl-1,3-di-(3-amino-2,4,6-triiodophenyl)-octanoate; glyceryl 2-oleoyl-1,3-di-(3-amino-2,4,6-triiodophenyl)-heptanoate (DHOG), etc. A detailed description of methods of making the aforementioned 1,3-disubstituted triacylglycerols is set forth in a co-pending patent application Ser. No. 08/243,596 filed on May 16, 1994.

For the studies reported herein, iodinated triglycerides were synthesized and radioiodinated with $^{125}$I via isotope exchange in a melt of pivalic acid in accordance with a method known in the art. Of course, radioiodination of the iodinated triglycerides, or one of the intermediates in their synthesis pathway, can be accomplished by a variety of techniques, known to those of skill in the art.

The following specific examples illustrate some of the many possible lipophilic contrast agents that can be delivered to the blood pool in oil-in-water emulsions made in accordance with the principles of the invention.

Example 1

Figure 1:
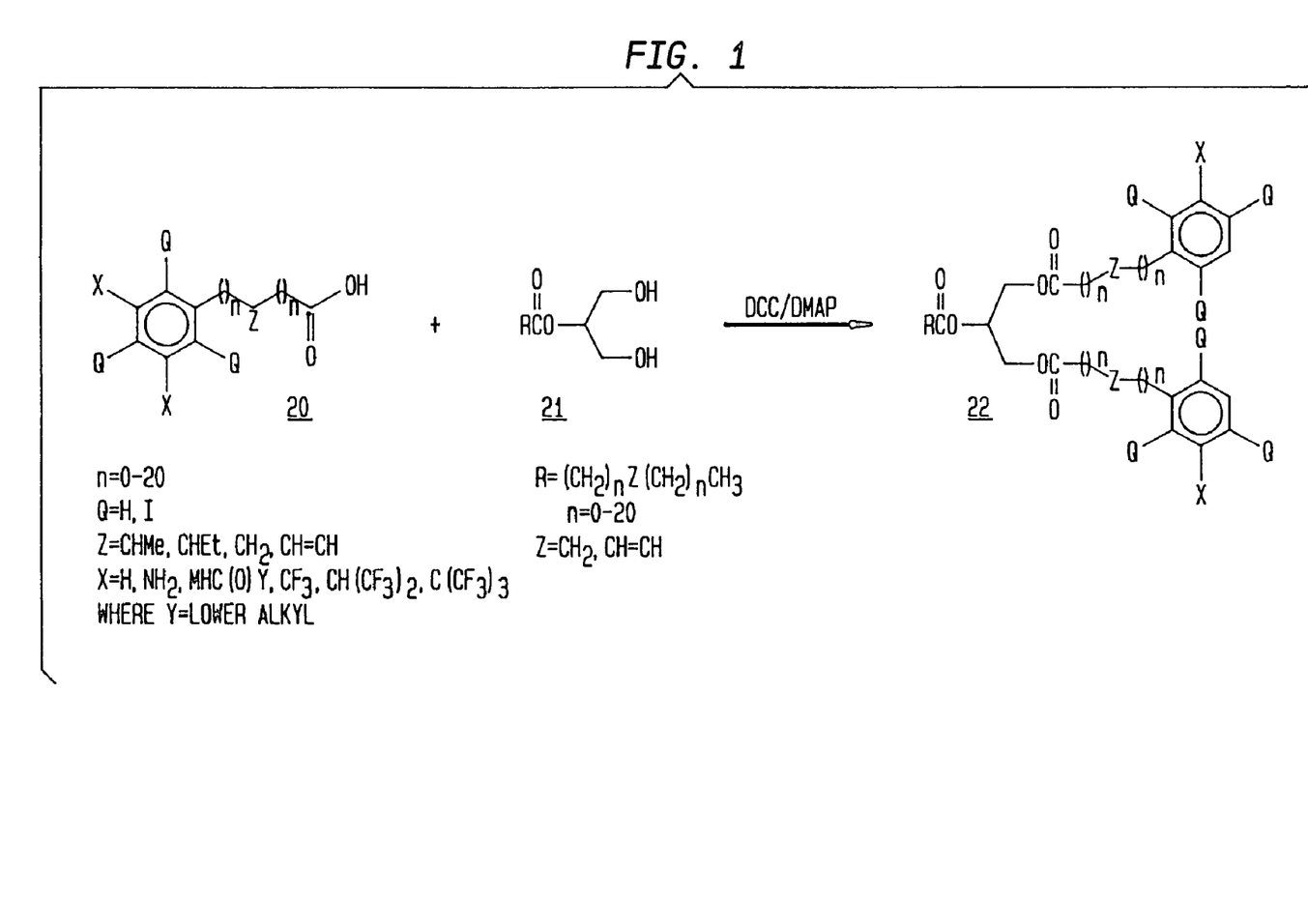
FIG. 1 is an illustrative preparatory scheme for a series of fluorinated or iodinated triglycerides, specifically 1,3-disubstituted triacylglycerols, suitable for use in the practice of the present invention.

Referring to FIG. 1, a general reaction scheme is shown for iodinated or fluorinated triglycerides, specifically 1,3-disubstituted triacylglycerols, or ω-(3-amino-2,4,6-triiodophenyl) alkanoates, suitable for use in the practice of the present invention (Compounds 22). In the illustrative embodiments of Example 1, Compounds 22 are 2-oleoylglycerol-1,3-bis-[3-amino-2,4,6-triiodophenyl)alkanoates] which were synthesized via dicyclohexylcarbodiimide/4-diethylaminopyridine (DCC/DMAP) coupling of a 2-monoolein (Compounds 21) with 2 equivalents of the corresponding ω-(3-amino-2,4,6-triiodophenyl)alkanoic acid (Compounds 20) as described below.

Preparation of ω-(3-amino-2,4,6-triiodophenyl)alkanoic acids

Synthesis of the ω-(3-amino-2,4,6-triiodophenyl)alkanoic acids (Compounds 20) was accomplished in a similar fashion to existing literature procedures (see, for example, Weichert, et al., *J. Med. Chem.*, Vol. 29, p. 1674 and 2457 (1986); and Vol. 38, p. 636 (1995). Iopanoic acid is commercially available and was purchased from CTC Organics, Atlanta, Ga.

Preparation of 2-oleoylglycerol-1,3-bis-[3-amino-2,4,6-triiodophenyl)alkanoates]

Figure 2:
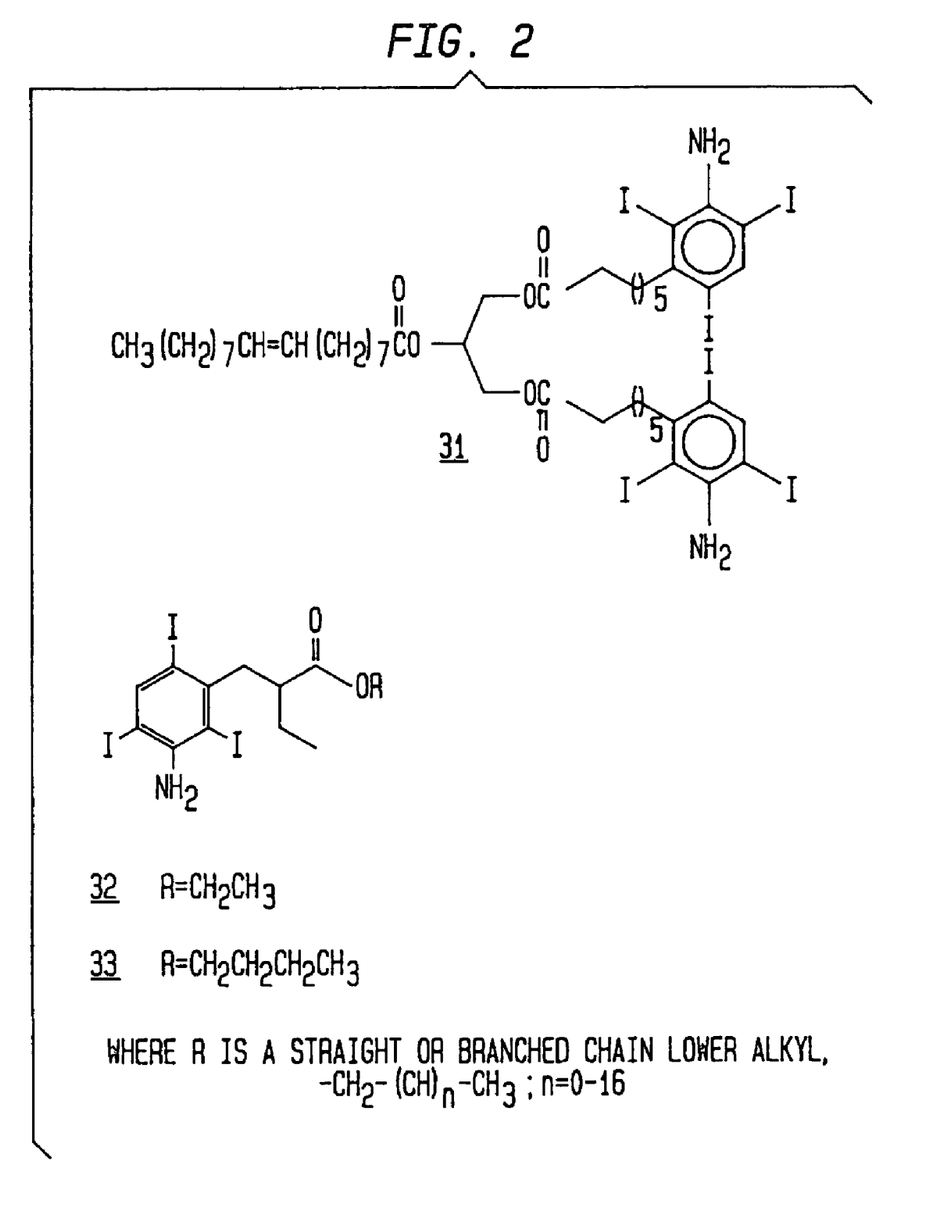
FIG. 2 shows molecular formulae for lipophilic triacylglycerols useful in the practice of the present invention.

A rapidly stirred suspension of the alcohol (2-monoolein; 1,2,3-trihydroxypropane 2-oleate; 1.0 equiv), the carboxylic acid (ω-(3-amino-2,4,6-triiodophenyl)alkanoic acids; 1-2.1 equiv), and a catalytic amount of DMAP (0.1 equiv) in anhydrous $CH_2Cl_2$ (5 ml/mmol of alcohol) was treated with DCC (1.1 equiv to acid). The resulting mixture was stirred under $N_2$ overnight at room temperature, diluted with $CH_2Cl_2$ and filtered to remove precipitated dicyclohexyl urea. The filtrate was washed with 0.5 N HCl, saturated aqueous $NaHCO_3$, $H_2O$, and brine, and then dried ($MgSO_4$). The solvent was removed in vacuo, and the remaining residue was purified by column chromatography to afford the desired esters, Compounds 31 to 33, shown on FIG. 2. Compound 31 is a specific example of Compounds 22 on FIG. 1.

2-oleoylglycerol-1,3-bis[7-(3-amino-2,4,6-triiodophenyl)heptanoate] (Compound 31)

DCC (3.62 g, 17.5 mmol) was added to a stirred suspension of 7-(3-amino-2,4,6-triiodophenyl)heptanoic acid (10.0 g, 16.7 mmol), 2-monoolein (2.83 g, 7.9 mmol), and DMAP (180 mg) in anhydrous $CH_2Cl_2$ (120 ml) according to the procedure described above for 24 hours. Following workup, a residue (14.7 g) was obtained, which was purified by column chromatography on silica gel (10×25 cm) eluted with hexanes/EtOAc/CHCl$_1$ (80:15:5) to give Compound 31, as shown on FIG. 2, as a slightly yellow oil that resisted crystallization: yield 9.45 g (79%); IR (CHCl$_1$) 3450, 3359 (amine), 2915, 2840 (aliphatic CH). 1740 (ester C=O) cm$^1$; $^1$H NMR (360 MHZ, CDCl$_1$) 8.03 (s, 2H, aryl 5-H's), 5.30 (m, 3H, CH=CH, and glycerol 2-H), 4.79 (s, 4H, $NH_2$), 4.31 (m, 2H, glycerol OCH$_4$H$_5$CH(O)CH$_4$H$_5$O), 4.16 (m, 2H, glycerol OCH$_4$H$_5$CH(O)CH$_4$H$_5$O), 3.00 (m, 4H, PhCH$_2$'s), 2.32 (m, 6H, O$_2$CCH$_1$'s and oleate O$_2$CCH$_2$), 2.00 (m, 4H, allylic CH$_2$'s), 1.72 (m, 4H, PhCH$_2$CH$_2$'s), 1.61-1.26 (m, CH$_2$ envelope), 0.88 (t, 3H, CH$_1$). Anal ($C_{47}H_{48}O_4N_2I_4$) C, H.

Ethyl Iopanote (Compound 32)

DCC (401 mg, 1.9 mmol) was added to a stirred suspension of iopanoic acid (1.02 g, 1.79 mmol), absolute ethanol (75 mg, 1.6 mmol), and DMAP (24 mg) in anhydrous $CH_2Cl_2$ (30 ml) according to the procedure described above for 24 hours. Following workup, a residue (900 mg) was obtained, which was purified by column chromatography on silica gel (6×25 cm) eluted with 1% EtOAc/CHCl$_3$ to give 801 mg of ethyl iopanoate (Compound 32) as a slightly yellow oil (75% yield).

Butyl Iopanoate (Compound 33)

DCC (476 mg, 2.3 mmol) was added to a stirred suspension of iopanoic acid (1.21 g, 2.1 mmol), n-butanol (143 mg, 1.9 mmol), and DMAP (28 mg) in anhydrous $CH_2Cl_2$ (30 ml) according to the procedure described above for 24 hours. Following workup, a residue (1.6 g) was obtained, which was purified by column chromatography on silica gel (6×25 cm) eluted with 1% EtOAc/CHCl$_3$ to give 1.08 g of butyl iopanoate (Compound 33) as a slightly yellow oil (91% yield).

The iodinated triglycerides of Example 1 were incorporated into the lipid core of an oil-in-water emulsion by formulation techniques in accordance with the invention as set forth more completely in the following examples.

Example 2

The general formula for a blood-pool selective oil-in-water emulsion in accordance with the present invention is as follows:

10% (w/v) Total Lipid (inert oil+contrast agent)
    e.g., triolein (TO)+DHOG
    TO:DHOG (w/w)=1:1
0.5% PEG Component
    methyl polyethylene glycol (2000)-distearoylphosphatidvlethanolamine (DSPE)
2.4% (w/v) Total Phospholipid
    e.g., DOPC [1.9% (w/v)]+MPEG-DSPE [0.5% (w/v)]
0.4% (w/v) Sterol
    e.g., cholesterol
    DOPC+MPEG-DSPE (molar ratio)=0.4
5% (w/v) USP glycerol
0.6% (w/v) α-tocopherol
parenteral grade, de-ionized water as bulk aqueous phase In specific illustrative embodiments, Compound 31, which is DHOG, and Compounds 32 and 33, are formulated into an oil-in-water emulsions in accordance with the methods set forth below:

Emulsion Example 1

DHOG (0.7507 g), triolein (0.7509 g), cholesterol (0.0613 g), α-tocopherol (0.0900 g) and MPEG-DSPE (0.0757 g) are weighed sequentially into a tared tube into which DOPC (0.2850 g) in ethanol solution is introduced. A 5 ml volume of chloroform is added to the tube to dissolve the lipid components. The solvents are removed in vacuo at 37° C. on a rotary evaporator, interrupting the process once to rinse down the tube with an additional 1.5 ml of CHCl$_3$. After completion of solvent removal, the tube is tared and anhydrous glycerol (0.7530 g) is added to the lipid mixture. The tube is positioned on a Polytron homogenizer for a 5 min preliminary emulsification at 12,500 rpm under a nitrogen atmosphere at 50-55° C. A 10 ml aliquot of sterile water is added with continuous mixing, followed by 5 min of emulsification at 25,000 rpm under the same conditions. The volume of the crude emulsion is adjusted to a final volume of 15 ml with additional sterile water. The preparation is transferred to a Model 110-S MicroFluidizer for final emulsification at 18,200 psi for 10 min between 54-55.8° C. The emulsion is then passed sequentially through sterile 0.45 mm and 0.2 mm filter units into a sterile multidose vial. The emulsion is equilibrated at room temperature prior to determining mean particle diameter by submicron laser photon correlation spectroscopy (PCS). Mean particle diameter is 74 nm.

Emulsion Example 2

Ethyl iopanoate (0.5044 g), triolein (0.5042 g), cholesterol (0.0410 g), α-tocopherol (0.0619 g) and MPEG-DSPE (0.0500 g) are weighed into a tared tube into which DOPC (0.1900 g) in ethanol solution is added. A 4 ml portion of $CHCl_3$ is added to the tube to dissolve the lipid mixture. The solvents are evaporated in vacuo at 37° C. as described in example 1. After evaporation of the solvents, anhydrous glycerol (0.5014 g) is added to the lipid mixture and emulsified for 5 min at 12,500 rpm on the Polytron under nitrogen. A 6 ml aliquot of sterile water is added with continuous mixing and emulsified at 25,000 rpm for 5 min at a temperature of approximately 55° C. The crude emulsion is transferred to the MicroFluidizer after dilution to a final volume of 10 ml with sterile water. The final emulsification is performed at 18,200 psi for 10 min at 49.2-50.9° C. The emulsion is passed through sterile filters into a sterile vial as described in example 1. The mean particle diameter determined by PCS sizing on the Nicomp 370 is approximately 80 nm.

Emulsion Example 3 n-Butyl iopanoate ((0.5037 g), triolein (0.5025 g), cholesterol (0.0416 g), α-tocopherol (0.0620 g) and MPEG-DSPE (0.0503 g) are weighed into a tared tube into which DOPC (0.1900 g) in ethanol solution is added. A 5 ml volume of $CHCl_3$ is added to the tube to dissolve the lipids. The solvents are evaporated in vacuo as described in example 1. After evaporation of the solvents, anhydrous glycerol (0.5009 g) is added to the tube containing the lipid mixture. The mixture is emulsified as described in example 1. The emulsion is transferred to the MicroFluidizer after dilution to a total volume of 10 ml with sterile water. Final emulsification is performed at 18,200 psi for 10 min at 50.8-51.5° C. The emulsion is filtered into a sterile multidose vial and equilibrated at room temperature. The mean particle diameter is approximately 83 nm as determined by PCS sizing.

Emulsion Example 4

A 20% blood-pool emulsion is prepared in the following manner. DHOG (1.6507 g), triolein (1.6507 g) cholesterol (0.0996 g), α-tocopherol (0.0994 g) and MPEG-DSPE (0.1245 g) are weighed sequentially into a tared tube into which DOPC (0.4700 g) in ethanol solution is introduced. A 5 ml volume of chloroform is added to the tube to dissolve the lipid components. The solvents are evaporated at 37° C. in vacuo as described in example 1. After evaporation of the solvents the tube is tared prior to addition of anhydrous glycerol (0.8266 g) to the lipid mixture. The tube is positioned on the Polytron to emulsify the mixture at 12,500 rpm for 5 min at less than 55° C. under a nitrogen atmosphere. A 10 ml aliquot of sterile water is added with continuous mixing prior to emulsification at 25,000 rpm under the same conditions. The emulsion is transferred to the MicroFluidizer after dilution to a total volume of 16.5 ml with sterile water. Final emulsification is performed at 18,600 psi for 5 min at 42.4-51.4° C. The emulsion is filtered into a sterile multidose vial and equilibrated at room temperature. The mean particle diameter is approximately 66.8 nm as determined by PCS sizing.

Emulsion Example 5

A radiolabeled form of the 10% blood-pool emulsion is prepared as follows. DHOG (0.5003 g), triolein (0.5008 g), cholesterol (0.0403 g), α-tocopherol (0.0604 g) and MPEG-DSPE (0.0501 g) are weighed sequentially into a tared tube into which DOPC (0.1900 g) in ethanol solution is introduced. A 5 ml volume of chloroform is added to the tube to dissolve the lipid components. The solvents are evaporated as described in example. A 0.25 ml aliquot of $^{125}$I-DHOG in $CHCl_3$ solution is added to the tube which is then rinsed down with additional $CHCl_3$ (1.2 ml). The chloroform is evaporated as before. The tube is tared and anhydrous glycerol (0.5008 g) is added to the tube which is then positioned on the Polytron. The mixture is emulsified under nitrogen at about 55° C. for 5 min at 12,500 rpm. A 6.5 ml aliquot of sterile water is added with continuous mixing and emulsified at 25,000 rpm for 5 min as described above. The emulsion is transferred to the MicroFluidizer 110-S for final emulsification at 18,200 psi for 10 min between 54.4-55.5° C. The emulsion is filtered through sterile filter units into a sterile multidose vial. The activity of the emulsion is 15.2 mCi/ml.

For comparative purposes, a radioactive lipid emulsion that does not contain the PEG moiety (DHOG-LE) was prepared as follows:

Emulsion Example 6 (Prior Art)

A radiolabeled form of the 10% DHOG emulsion is prepared as follows. DHOG (0.5004 g), triolein (0.5003 g), cholesterol (0.0472 g) and α-tocopherol (0.0601 g) are weighed sequentially into a tared tube into which DOPC (0.2400 g) in ethanol solution is introduced. A 4.8 ml volume of ethyl acetate is added to the tube to dissolve the lipid components. The solvents are evaporated as described in example. A 0.25 ml aliquot of $^{125}$I-DHOG in $CHCl_3$ solution is added to the tube which is then rinsed down with 1.0 ml ethyl acetate:ethanol, (2:1, v/v). The solvents are evaporated as before. The tube is tared and anhydrous glycerol (0.5012 g) is added to the tube which is then positioned on the Polytron. The mixture is emulsified under nitrogen at about 55° C. for 5 min at 12,500 rpm. A 6.5 ml aliquot of sterile water is added with continuous mixing and emulsified at 25,000 rpm for 5 min as described above. The emulsion is transferred to the MicroFluidizer 110-S for final emulsification at 18,200 psi for 10 min between 33.5-36.4° C. The emulsion is filtered through sterile filter units into a sterile multidose vial. The activity of the emulsion is 15.7 mCi/ml.

Emulsion Example 7

A 30% blood-pool emulsion is prepared in the following manner: DHOG (2.4751 g), triolein (2.4756 g), cholesterol (0.1321 g), α-tocopherol (0.0995 g) and 1,2-distearoyl-sn-glycero-3-phosphoethanolamine-N-[poly(ethylene glycol)-2000] (MPEG-DSPE 2000; 0.1657 g) are weighed sequentially into a tared tube into which DOPC (0.6262 g) in ethanol solution is introduced. A 5 ml volume of chloroform is added to the tube to dissolve the lipid components. The solvents are evaporated at 37° C. in vacuo as described in example 1. After evaporation of the solvents the tube is tared prior to addition of anhydrous glycerol (0.8265 g) to the lipid mixture. The tube is positioned on the Polytron to emulsify the mixture at 12,500 rpm for 5 minutes at less than 55° C. under a nitrogen atmosphere. A 9 ml aliquot of sterile water is added to the anhydrous emulsion with continuous mixing prior to further emulsification at 25,000 rpm for 5 minutes under the same conditions. The emulsion is transferred to the MicroFluidizer after dilution to a total volume of 16.5 ml with sterile water. Final emulsification is performed at 17,000 psi for 5 min at 43.1-55.2° C. The emulsion is sequentially filtered through sterile 0.45 μm ns 0.2 μm filter assemblies into a sterile multidose vial and equilibrated at room temperature. The mean particle diameter is approximately 96 nm as determined by PCS sizing.

Example 3

Biodistribution Studies

Radioactive emulsions of the iodinated triglyceride DHOG was prepared by the technique set forth in Emulsion Example 5 (DHOG-PEG) and the corresponding hepatocyte-selective form of Emulsion Example 6 (DHOG-LE).

Figure 3:
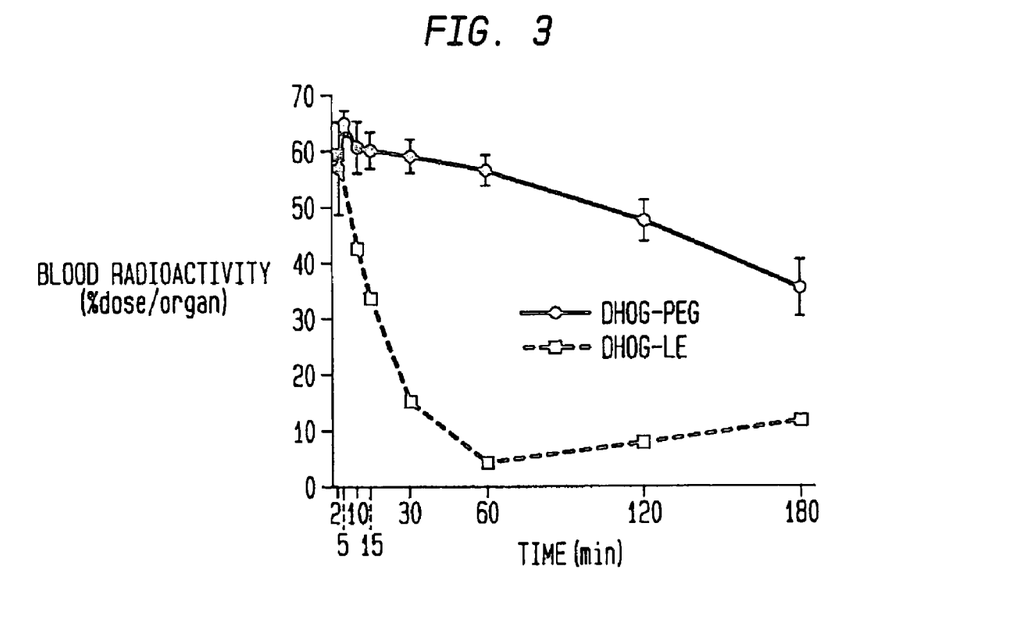
FIG. 3 is a graphical representation of blood radioactivity in % dose/organ versus time in minutes following iv administration of DHOG-LE or DHOG-PEG to female Sprague-Dawley rats (n=3)

The emulsions were administered intravenously (tail vein) to normal female Sprague-Dawley rats at a radiologic dose of 50 mg 1/kg body weight for biodistribution studies. Blood samples were drawn and analyzed for radioactivity prior to and at predetermined intervals following iv administration of the agent. The results of this pharmacokinetics study are shown in FIG. 3 which is a graphical representation of blood radioactivity in % dose/organ versus time in minutes following iv administration of DHOG-LE or DHOG-PEG to female Sprague-Dawley rats (n=3).

Hepatic clearance of DHOG-LE from the blood is rapid and by 60 minutes only about 5% of the injected dose remains in the blood. From 1 to 3 hours there is a slight increase in blood level which is probably associated with hepatic repackaging into other lipoproteins and subsequent release back into the bloodstream. Blood radioactivity remains elevated for up to 2-3 hours following administration of DHOG-PEG under identical conditions. At one hour following administration, for example, over 56% of the administered DHOG-PEG remains in the blood as compared to only 4.2% of the hepatocyte-selective DHOG-LE emulsion.

In another study, tissue distribution results were obtained by administering the radiolabeled DHOG-PEG of Emulsion Example 5 (17 μCi/ml, 5 μCi/animal) to female Sprague-Dawley rats (178-218 grams). The rats were exsanguinated at predetermined time points (n=3 for each time point) following injection of the radiolabeled emulsion into the tail vein. A total of thirteen tissues were excised, minced, weighed, and analyzed for radioactivity with a gamma counter. The results are presented in Table 1 as either % injected dose/gram of tissue (concentration) or as % injected dose/organ (blood, liver, spleen) at the following time points: 5 min., 30 min., 1 hour, 3 hours, and 24 hours.

TABLE 1

| Tissue | 5 MIN. | 30 MIN. | 1 HOUR | 3 HOUR | 24 HOUR |
|---|---|---|---|---|---|
| | | | % Dose/G | | |
| Adrenal | 0.533 ± 0.024 | 1.194 ± 0.187 | 1.66 ± 0.512 | 1.999 ± 0.676 | 0.401 ± 0.048 |
| Blood | 6.717 ± 0.156 | 6.334 ± 0.123 | 5.771 ± 0.215 | 4.575 ± 0.277 | 0.190 ± 0.018 |
| Bone Marrow | 0.846 ± 0.049 | 1.036 ± 0.300 | 0.654 ± 0.028 | 0.695 ± 0.043 | 0.095 ± 0.010 |
| Fat | 0.072 ± 0.016 | 0.084 ± 0.017 | 0.66 ± 0.006 | 0.129 ± 0.056 | 0.027 ± 0.004 |
| Heart | 0.583 ± 0.021 | 0.667 ± 0.062 | 0.596 ± 0.057 | 0.584 ± 0.049 | 0.094 ± 0.001 |
| Kidney | 0.744 ± 0.098 | 0.715 ± 0.053 | 0.667 ± 0.036 | 0.654 ± 0.025 | 0.233 ± 0.010 |
| Liver | 0.576 ± 0.027 | 0.781 ± 0.097 | 0.597 ± 0.060 | 1.126 ± 0.217 | 0.851 ± 0.057 |
| Lung | 0.776 ± 0.029 | 0.714 ± 0.019 | 0.688 ± 0.055 | 0.586 ± 0.022 | 0.071 ± 0.005 |
| Muscle | 0.058 ± 0.007 | 0.086 ± 0.003 | 0.056 ± 0.012 | 0.062 ± 0.005 | 0.023 ± 0.003 |
| Ovary | 0.445 ± 0.042 | 0.582 ± 0.045 | 0.502 ± 0.116 | 0.850 ± 0.234 | 0.247 ± 0.038 |
| Plasma | 11.201 ± 0.282 | 10.780 ± 0.481 | 9.908 ± 0.375 | 7.651 ± 0.373 | 0.168 ± 0.016 |
| Spleen | 0.842 ± 0.003 | 1.399 ± 0.023 | 1.602 ± 0.186 | 1.717 ± 0.026 | 0.356 ± 0.021 |
| Thyroid | 0.521 ± 0.041 | 0.800 ± 0.066 | 1.082 ± 0.158 | 1.388 ± 0.146 | 6.795 ± 0.827 |
| | | | % Dose/Organ | | |
| Blood | 61.506 ± 1.560 | 58.879 ± 1.576 | 60.351 ± 0.842 | 48.025 ± 1.865 | 1.716 ± 0.127 |
| Liver | 4.708 ± 0.174 | 6.302 ± 0.517 | 5.351 ± 0.253 | 11.432 ± 2.588 | 5.396 ± 0.148 |
| Spleen | 0.398 ± 0.050 | 0.697 ± 0.022 | 0.923 ± 0.088 | 0.737 ± 0.008 | 0.153 ± 0.002 |

The results shown on Table 1 demonstrate that the surface-modified emulsion of the present invention remains in the blood for over three hours. By 24 hours, however, the blood radioactivity of DHOG-PEG approaches baseline. This is in sharp contrast to the hepatocyte-selective version which is cleared from the blood in less than 30 minutes as it is sequestered in the liver (See FIG. 3 and Table 2 which shows the results of a similar tissue distribution study conducted with DHOG-LE). The differences between blood, plasma, liver and spleen levels are striking. These results demonstrate that the PEG surface-modification significantly influences the pharmacodynamic profile of the iodinated triglyceride molecule.

TABLE 2

| Tissue | 30 MIN. | 3 HOUR | 24 HOUR |
|---|---|---|---|
| | | % Dose/G | |
| Adrenal | 0.871 ± 0.154 | 0.761 ± 0.241 | 0.213 ± 0.045 |
| Blood | 0.584 ± 0.284 | 0.282 ± 0.287 | 0.218 ± 0.052 |
| Bone Marrow | 0.273 ± 0.066 | 0.270 ± 0.072 | 0.078 ± 0.013 |
| Fat | 0.134 ± 0.046 | 0.069 ± 0.003 | 0.044 ± 0.006 |
| Heart | 0.547 ± 0.125 | 0.222 ± 0.039 | 0.101 ± 0.006 |

TABLE 2-continued

| Tissue | 30 MIN. | 3 HOUR | 24 HOUR |
|---|---|---|---|
| Kidney | 0.204 ± 0.025 | 0.180 ± 0.037 | 0.216 ± 0.047 |
| Liver | 7.228 ± 0.726 | 5.837 ± 0.579 | 1.105 ± 0.197 |
| Lung | 0.657 ± 0.142 | 0.342 ± 0.041 | 0.293 ± 0.021 |
| Muscle | 0.051 ± 0.044 | 0.170 ± 0.046 | 0.113 ± 0.016 |
| Ovary | 0.240 ± 0.044 | 0.170 ± 0.046 | 0.113 ± 0.016 |
| Plasma | 0.832 ± 0.504 | 0.285 ± 0.039 | 0.211 ± 0.036 |
| Spleen | 21.796 ± 5.870 | 15.345 ± 2.852 | 1.431 ± 0.634 |
| Thyroid | 0.312 ± 0.020 | 1.685 ± 0.114 | 6.525 ± 0.641 |
| % Dose/Organ | | | |
| Blood | 6.582 ± 3.063 | 2.760 ± 0.347 | 2.479 ± 0.609 |
| Liver | 67.667 ± 6.521 | 45.840 ± 2.544 | 9.634 ± 1.267 |
| Spleen | 10.514 ± 2.085 | 8.193 ± 1.017 | 0.767 ± 0.272 |

In Vivo Imaging Studies

Figure 4:
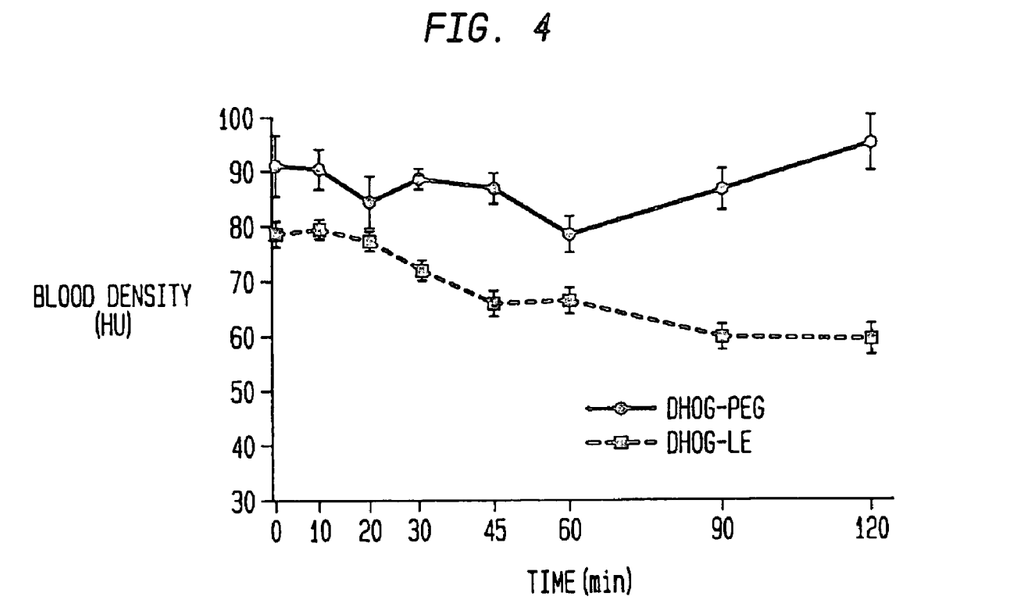
FIG. 4 is a graphical representation of CT density in Hounsfield Units (HU) versus time in minutes in the blood of female New Zealand White rabbits following iv administration of DHOG-PEG or DHOG-LE.

Computed tomography studies were conducted in normal female New Zealand White rabbits using the DHOG-PEG and DHOG-LE emulsions of Emulsion Example 1 and the corresponding non-radioactive form of Emulsion Example 6. The results are shown in FIG. 4 which is a graphical representation of CT density in Hounsfield Units (HU) versus time in minutes in the blood of female New Zealand White rabbits following iv administration of DHOG-PEG or DHOG-LE. Blood-pool density enhancement was sustained for DHOG-PEG relative to DHOG-LE. Blood levels remained elevated up to 2 hours post-administration. However, follow-up CT studies, completed 24 hours after the initial administration, revealed that blood levels had dropped essentially to baseline.

Pulmonary Hypertension Studies

In order to assess the effect of a blood-pool selective oil-in-water emulsion on hemodynamic parameters, the emulsion of Emulsion Example 1, which is a 10% emulsion of iodinated DHOG (60 mg I/kg), was administered to a pig. Swine serve as an indicator of particulate-induced pulmonary hypertension because they have an unusually high number of RES cells in their lungs.

Pressure transducers were placed in the right pulmonary artery and the abdominal aorta of a female pig (21 kg). Heart rate was monitored with an EKG. Anesthesia was initially induced with Telazol (7 mg/kg)/Xylazine (2.2 mg/kg) IM and subsequently maintained with Halothane. The emulsion was administered intravenously through the ear vein at a rate of 10 ml/min, over a period of 5 minutes, followed by a 10 ml normal saline flush. Pressure and heart rate were measured every minute for the first 15 minutes following injection, and then every 5 minutes until 90 minutes post-injection. The results are shown on FIG. 5 which is a graphical representation of pulmonary artery pressure and heart rate with respect to time (in minutes) post-injection.

Figure 5:
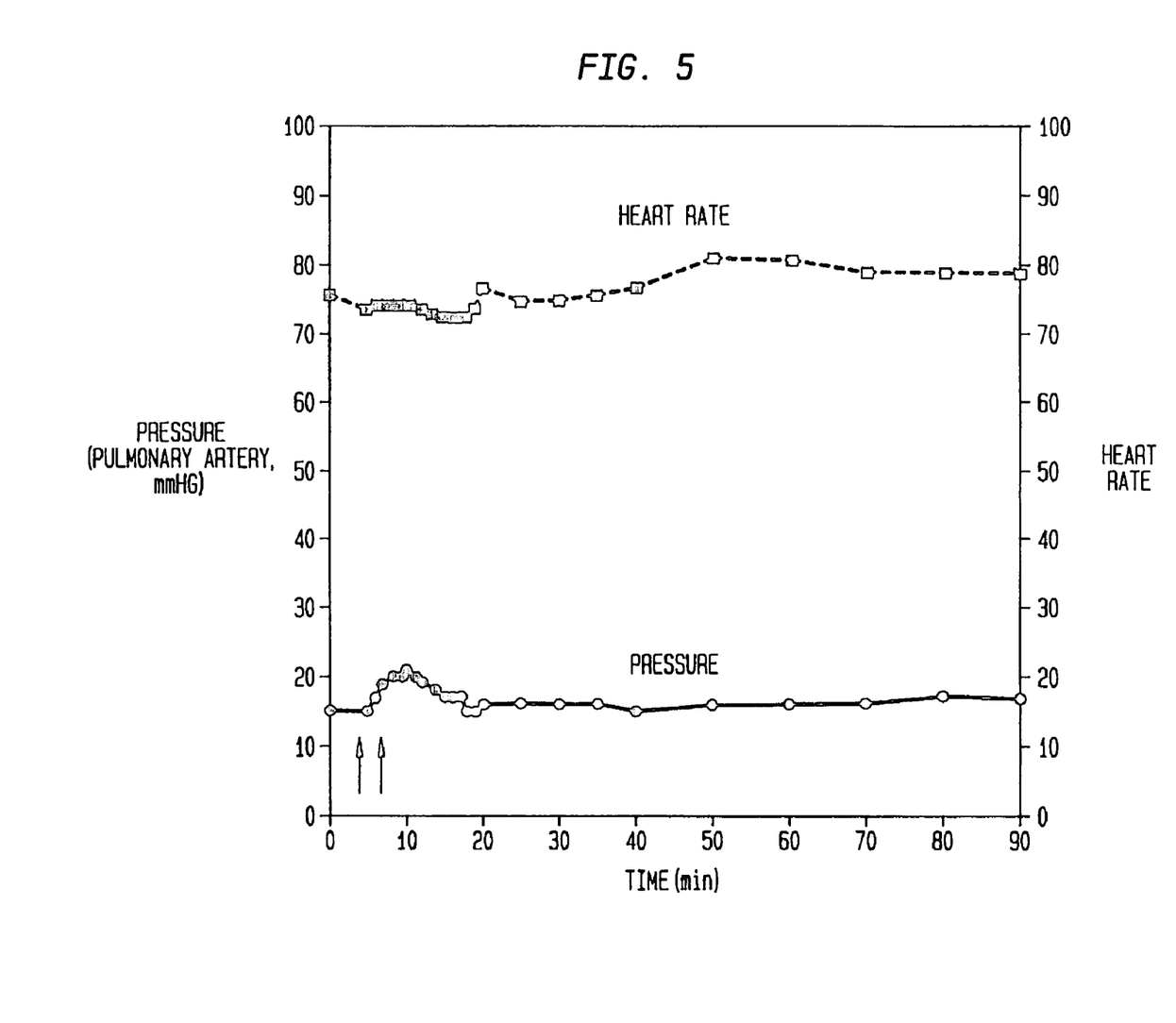
FIG. 5 is a graphical representation of pulmonary artery pressure and heart rate as a function of time (in minutes) post-administration of a contrast-agent containing emulsion of present invention to a pig.

Referring to FIG. 5, the arrows indicate the start of injection and the end point. Heart rate was not affected and pulmonary pressure was only transiently elevated (4-5 mm Hg) during the injection phase and immediately returned to baseline levels. This is indicative that the emulsion of the present invention does not effect hemodynamic parameters.

Example 4

In a particularly advantageous embodiment of the invention, a hepatocyte-selective oil-in-water emulsion is co-administered with the blood-pool agent of the present invention. Liver-selective particulate agents (hepatocyte-selective or Kupffer cell-selective) clear rapidly from the blood and render the blood hypodense relative to surrounding liver tissue. It is very difficult to separate small tumors, which also appear as hypodense areas from small vasculature in the sub 5 mm size range. In order to compensate for this problem, DHOG-PEG (Example 1) and hepatocyte-selective DHOG-LE (Emulsion Example 6, non-radioactive form) were co-administered to rabbits bearing VX2 tumors.

Rabbits (mean weight 2.5 kg) were inoculated with VX2 carcinoma directly into the hepatic parenchyma to produce a total of 8 focal lesions (2-10 mm). Ten days later, the rabbits were scanned with multiple techniques including noncontrast, helical IV enhanced (600 mg I/kg iohexol), and 24 hours later using the iodinated microparticulate emulsion (200 mg I/kg). Tissue density measurements (HU) were made of liver, lesions, and blood (descending aorta). Tumor morphology was verified by gross pathologic examination.

Pharmacokinetic analysis, as well as CT studies, revealed that the blood-pool agent of the present invention remains in the blood-pool phase for more than 2 hours following IV administration. In fact, blood density in a normal rabbit was 95.1±5.8 HU at 120 minutes compared to 90.7±6.1 HU immediately after injection.

Normal liver enhancement with emulsions yielded a slightly more granular pattern than with iohexol. Intrahepatic vasculature was well enhanced (aorta=127.4 HU at 64 minutes post-injection). Tumors were significantly enhanced with iohexol (+40.1 HU) in contrast to emulsions (+2.3 HU, $p<0.051$). Enhancement of liver tissue was greater for iohexol (+66.8 HU) than for the emulsions (+31.6 HU), but the liver-to-lesion difference favored the emulsions due to the lack of tumor enhancement (31.8 versus 28.8). The lesions were subjectively better delineated with the emulsions due to sharper edge definition.

TABLE 3

| Technique | Lesions < 1 cm | Lesions > 1 cm | Overall |
|---|---|---|---|
| non-contrast | 33.3 | 83.3 | 51.5 |
| iv iohexol | 49.3 | 97.6 | 67.6 |
| ITG blood pool Only | 68.5 | 87.5 | 75.6 |
| Combination | 72.2 | 95.2 | 80.7* |

*$p < 0.05$ versus iohexol

The results set forth in the Table 3 indicate that the combination opacified both the liver cells and the blood to improve both sensitivity and confidence in detection of very small tumors. It should be noted that the receptor-mediated, hepatocyte-selective emulsion DHOG-LE enhances the liver significantly within 15-30 minutes post-injection. Blood-pool enhancement occurs transiently following iv administration of the hepatocyte-selective formulation and then diminishes rapidly as the agent is sequestered by the liver. The blood-pool agent of the present invention does not enhance the liver for the first two hours following injection. Therefore, co-administration of a hepatocyte-selective lipid emulsion with the blood-pool lipid selective emulsion of the present invention advantageously results in enhancement of the normal liver parenchyma and hepatic/systemic vasculature without significant tumor enhancement.

Although the foregoing examples related to vehicles and/or contrast agents useful for CT imaging, lipophilic agents, or lipophilic derivatives of water-soluble agents, useful in other imaging modalities, such as MRI agents, ultrasound agents, or radiopharmaceuticals, are within the contemplation of the invention.

The oil-in-water emulsions of the present invention are suitable for parenteral administration to a mammalian subject, typically by intravenous administration. However, intramuscular, subcutaneous, intraperitoneal, and other delivery routes are within the contemplation of the invention. Further, the oil-in-water emulsions of the present invention may be administered by other routes, such as oral. It is a specific advantage of the oil-in-water emulsions of the present invention that they may be administered intravenously versus arterially, and in doses small enough, and slow enough, to be well-tolerated. Anticipated dose levels are 20 to 250 mg I/kg body weight.

In a method of use aspect of the invention, blood-pool imaging not only offers diagnostic potential for virtually all vascular diseases including atherosclerosis and aneurysms, but also has potential to demonstrate organ perfusion defects. Moreover, new advances in CT scanner technology, namely the introduction of ultra fast electron-beam CT scanners, may render this agent directly useful for cardiac angiography without the need for invasive and costly catheterization procedures.

Further it should be noted that the animal models selected and used in the studies presented hereinabove, specifically rats and rabbits, are well known to have hepatic physiologies that closely resemble the hepatic physiology of humans. Moreover, the blood-pool selective oil-in-water emulsions of the present invention afforded no adverse response in the pig pulmonary hypertension model.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A surface-modified lipoprotein-like oil-in-water emulsion having a lipophilic core surrounded by a monolayer of amphiphilic or polar lipids, in a non-ionic aqueous phase, the emulsion having a mean particle diameter of the oil phase of between 50 to 150 nm with at least 98% of the particles being between 50 to 250 nm, the lipophilic core including at least one pharmacologically inert nonpolar lipid and at least one lipophilic contrast agent, and the monolayer including an emulsifier, a derivatized polyethylene glycol, and a sterol, wherein the lipophilic core comprises between about 10% and 40% (w/v) of the total emulsion composition.

2. The oil-in-water emulsion of claim 1 wherein the at least one lipophilic contrast agent is a water-soluble contrast agent derivatized with a lipophilic moiety.

3. The oil-in-water emulsion of claim 1 wherein the at least one lipophilic contrast agent is a pharmaceutically acceptable nonpolar lipid.

4. The oil-in-water emulsion of claim 3 wherein the pharmaceutically acceptable nonpolar lipid is a triglyceride.

5. The oil-in-water emulsion of claim 4 wherein the triglyceride is a biocompatible oil of animal or vegetable origin.

6. The oil-in-water emulsion of claim 4 wherein the triglyceride is a synthetic or semi-synthetic lipid.

7. The oil-in-water emulsion of claim 6 wherein the triglyceride is a halogenated triglyceride.

8. The oil-in-water emulsion of claim 7 wherein the triglyceride is 2-oleoylglycerol-1,3-bis[7-(3-amino-2,4,6-triiodophenyl)heptanoate].

9. The oil-in-water emulsion of claim 1 wherein the pharmacologically inert nonpolar lipid is triolein.

10. The oil-in-water emulsion of claim 1 wherein the ratio of pharmacologically inert nonpolar lipid to contrast agent ranges from about 0.1:1.0 to 2:1 on a weight to weight basis.

11. The oil-in-water emulsion of claim 10 wherein the ratio of pharmacologically inert nonpolar lipid to contrast agent is 1:1 on a weight to weight basis.

12. The oil-in-water emulsion of claim 1 wherein up to 10% (w/v) of the emulsion is an amphipathic or polar lipid.

13. The oil-in-water emulsion of claim 12 wherein the amphipathic or polar lipid is an emulsifier.

14. The oil-in-water emulsion of claim 13 wherein the emulsifier is a natural, synthetic, or semi-synthetic phospholipid.

15. The oil-in-water emulsion of claim 14 wherein the phospholipid is synthetic or semi-synthetic.

16. The oil-in-water emulsion of claim 15 wherein the phospholipid is dioleoylphosphatidylcholine.

17. The oil-in-water emulsion of claim 14 wherein the phospholipid is soy lecithin.

18. The oil-in-water emulsion of claim 1 wherein up to 5% (w/v) of the emulsion is a sterol.

19. The oil-in-water emulsion of claim 18 wherein the sterol is cholesterol.

20. The oil-in-water emulsion of claim 18 wherein between about 0.4 to 0.5% (w/v) of the emulsion is a sterol.

21. The oil-in-water emulsion of claim 20 wherein the molar ratio of cholesterol to emulsifier is between 0.05 to 0.70.

22. The oil-in-water emulsion of claim 1 wherein the emulsion further includes a up to 5% (w/v) of an osmolality adjusting agent.

23. The oil-in-water emulsion of claim 22 wherein the osmolality adjusting agent is anhydrous glycerol.

24. The oil-in-water emulsion of claim 1 further comprising a sufficient amount of an antioxidant.

25. The oil-in-water emulsion of claim 24 wherein the antioxidant is α-tocopherol.

26. The oil-in-water emulsion of claim 1 wherein the derivatized polyethylene glycol comprises a linked lipid.

27. The oil-in-water emulsion of claim 1 wherein the emulsion comprises up to about 5% (w/v) derivatized polyethylene glycol.

28. The oil-in-water emulsion of claim 27 wherein the derivatized polyethylene glycol comprises between about 0.1 and 30 mole percent of the monolayer components.

29. The oil-in-water emulsion of claim 27 wherein the derivatized polyethylene glycol is selected from the group consisting of MPEG-linked phosphatidylethanolamine, MPEG-2000-1,2-distearoyl and MPEG-2000-1,2-dioleoyl phosphatidylethanolamine.

30. The oil-in-water emulsion of claim 27 wherein the derivatized polyethylene glycol comprises a methoxy polyethylene glycol moiety having a molecular weight between about 1000 and 6000.

31. A method of computerized tomographic imaging comprising the steps of:
   a) administering an imaging amount of the oil-in-water emulsion of claim 1 to a mammal, wherein said lipophilic core of the oil-in-water emulsion comprises a computerized tomography imaging agent; and
   b) when the imaging amount of the oil-in-water emulsion has reached the site to be imaged, carrying out computerized tomographic imaging of the site.

32. A surface-modified lipoprotein-like oil-in-water emulsion having a lipophilic core surrounded by a monolayer comprising up to about 10% (w/v) of an amphiphilic or polar lipid, in a non-ionic aqueous phase, the emulsion having a mean particle diameter of the oil phase of between 50 to 150 nm with at least 98% of the particles being between 50 to 250 nm, the lipophilic core including at least one lipophilic agent, and the monolayer including an emulsifier, a derivatized polyethylene glycol, and a sterol, wherein the lipophilic core comprises between about 10% and 40% (w/v) of the total emulsion composition.

33. The oil-in-water emulsion of claim 32 wherein the at least one lipophilic agent is a water-soluble contrast agent derivatized with a lipophilic moiety.

34. The oil-in-water emulsion of claim 32 wherein the at least one lipophilic agent is diagnostically or therapeutically active.

35. The oil-in-water emulsion of claim 32 wherein the at least one lipophilic agent is diagnostically active.

36. The oil-in-water emulsion of claim 32 wherein the at least one lipophilic agent is therapeutically active.

37. The oil-in-water emulsion of claim 32 wherein the at least one lipophilic agent is a pharmaceutically acceptable nonpolar lipid.

38. The oil-in-water emulsion of claim 37 wherein the pharmaceutically acceptable nonpolar lipid is a triglyceride.

39. The oil-in-water emulsion of claim 38 wherein the triglyceride is a biocompatible oil of animal or vegetable origin.

40. The oil-in-water emulsion of claim 38 wherein the triglyceride is a synthetic or semi-synthetic lipid.

41. The oil-in-water emulsion of claim 40 wherein the synthetic or semi-synthetic lipid is triolein.

42. The oil-in-water emulsion of claim 40 wherein the triglyceride is a halogenated triglyceride.

43. The oil-in-water emulsion of claim 42 wherein the triglyceride is 2-oleoylglycerol-1,3-bis[7-(3-amino-2,4,6-tri-iodophenyl)heptanoate].

44. The oil-in-water emulsion of claim 32 wherein the lipophilic core comprises at least one pharmacologically inert nonpolar lipid and a lipophilic contrast agent.

45. The oil-in-water emulsion of claim 44 wherein the lipophilic core comprises at least one pharmaceutically acceptable nonpolar lipid and the contrast agent is a halogenated triglyceride.

46. The oil-in-water emulsion of claim 44 wherein the ratio of pharmacologically inert nonpolar lipid to contrast agent ranges from about 0.1:1.0 to 2:1 on a weight to weight basis.

47. The oil-in-water emulsion of claim 46 wherein the ratio of pharmacologically inert nonpolar lipid to contrast agent is 1:1 on a weight to weight basis.

48. The oil-in-water emulsion of claim 32 wherein the amphipathic or polar lipid is an emulsifier.

49. The oil-in-water emulsion of claim 32 wherein the emulsifier is a natural, synthetic, or semi-synthetic phospholipid.

50. The oil-in-water emulsion of claim 49 wherein the phospholipid is synthetic or semi-synthetic.

51. The oil-in-water emulsion of claim 49 wherein the phospholipid is soy lecithin.

52. The oil-in-water emulsion of claim 50 wherein the phospholipid is dioleoylphosphatidylcholine.

53. The oil-in-water emulsion of claim 32 wherein up to 5% (w/v) of the emulsion is a sterol.

54. The oil-in-water emulsion of claim 53 wherein the sterol is cholesterol.

55. The oil-in-water emulsion of claim 54 wherein between about 0.4 to 0.5% (w/v) of the emulsion is a sterol.

56. The oil-in-water emulsion of claim 55 wherein the molar ratio of cholesterol to emulsifier is between 0.05 to 0.70.

57. The oil-in-water emulsion of claim 32 wherein the emulsion further includes up to 5% (w/v) of an osmolality adjusting agent.

58. The oil-in-water emulsion of claim 57 wherein the osmolality adjusting agent is anhydrous glycerol.

59. The oil-in-water emulsion of claim 32 further comprising a sufficient amount of an antioxidant.

60. The oil-in-water emulsion of claim 58 wherein the antioxidant is α-tocopherol.

61. The oil-in-water emulsion of claim 58 wherein the derivatized polyethylene glycol comprises a linked lipid.

62. The oil-in-water emulsion of claim 32 wherein the emulsion comprises up to about 5% (w/v) derivatized polyethylene glycol.

63. The oil-in-water emulsion of claim 62 wherein the derivatized polyethylene glycol comprises between about 0.1 and 30 mole percent of the monolayer components.

64. The oil-in-water emulsion of claim 62 wherein the derivatized polyethylene glycol is selected from the group consisting of MPEG-linked phosphatidylethanolamine, MPEG-2000-1,2-distearoyl and MPEG-2000-1,2-dioleoyl phosphatidylethanolamine.

65. The oil-in-water emulsion of claim 62 wherein the derivatized polyethylene glycol is methoxy polyethylene glycol having a molecular weight between about 1000 and 6000.

66. A surface-modified lipoprotein-like oil-in-water emulsion having a lipophilic core surrounded by a monolayer of amphiphilic or polar lipids, in a non-ionic aqueous phase, the emulsion having a mean particle diameter of the oil phase of between 50 to 150 nm with at least 98% of the particles being between 50 to 250 nm, the lipophilic core including at least one lipophilic radiologic contrast agent, and the monolayer including an emulsifier, a derivatized polyethylene glycol, and a sterol, wherein the lipophilic core comprises between about 10% and 40% (w/v) of the total emulsion composition.

67. The oil-in-water emulsion of claim 66, wherein said contrast agent is selected from a group consisting of an X-ray contrast agent, a CT contrast agent, and an MRI contrast agent.

68. The oil-in-water emulsion of claim 67, wherein said contrast agent is an X-ray contrast agent.

69. The oil-in-water emulsion of claim 67, wherein said contrast agent is a CT contrast agent.

70. The oil-in-water emulsion of claim 67, wherein said contrast agent is an MRI contrast agent.

71. The oil-in-water emulsion of claim 66, wherein said contrast agent is a water-soluble contrast agent derivatized with a lipophilic moiety.

72. The oil-in-water emulsion of claim 66, wherein said contrast agent is a pharmaceutically acceptable nonpolar lipid.

73. The oil-in-water emulsion of claim 72, wherein the pharmaceutically acceptable nonpolar lipid is a triglyceride.

74. The oil-in-water emulsion of claim 73, wherein the triglyceride is a synthetic or semi-synthetic lipid.

75. The oil-in-water emulsion of claim 74, wherein the triglyceride is a halogenated triglyceride.

76. The oil-in-water emulsion of claim 75, wherein the triglyceride is 2-oleoylglycerol-1,3-bis[7-(3-amino-2,4,6-tri-iodophenyl)heptanoate].

77. The oil-in-water emulsion of claim 66, wherein up to 5% (w/v) of the emulsion is a sterol.

78. The oil-in-water emulsion of claim 77, wherein between about 0.4 to 0.5% (w/v) of the emulsion is a sterol.

79. The oil-in-water emulsion of claim 78, wherein the sterol is cholesterol and the molar ratio of cholesterol to emulsifier is between 0.05 to 0.70.

80. The oil-in-water emulsion of claim 66, wherein the emulsion further includes up to 5% (w/v) of an osmolality adjusting agent.

81. The oil-in-water emulsion of claim 79, wherein the osmalality adjusting agent is anhydrous glycerol.

82. The oil-in-water emulsion of claim 66, further comprising a sufficient amount of an antioxidant.

83. The oil-in-water emulsion of claim 82, wherein the antioxidant is α-tocopherol.

84. The oil-in-water emulsion of claim 66, wherein the derivatized polyethylene glycol comprises a linked lipid.

85. The oil-in-water emulsion of claim 66, wherein the emulsion comprises up to about 5% (w/v) derivatized polyethylene glycol.

86. The oil-in-water emulsion of claim 85, wherein the derivatized polyethylene glycol comprises between about 0.1 and 30 mole percent of the monolayer components.

87. The oil-in-water emulsion of claim 85, wherein the derivatized polyethylene glycol is selected from the group consisting of MPEG-linked phosphatidylethanolamine, MPEG-2000-1,2-distearoyl and MPEG-2000-1,2-dioleoyl phosphatidylethanolamine.

88. The oil-in-water emulsion of claim 85, wherein the derivatized polyethylene glycol is methoxy polyethylene glycol having a molecular weight between about 1000 and 6000.

89. The oil-in-water emulsion of claim 66, wherein the emulsifier is soy lecithin.

90. The oil-in-water emulsion of claim 66, wherein the lipophilic core further comprises at least one triolein moiety, and the monolayer comprises dioleoylphosphatidylcholine, MPEG-2000-1,2-dioleoyl phosphatidylethanolamine and cholesterol.

\* \* \* \* \*